United States Patent [19]

Lalin

[11] Patent Number: 4,576,054

[45] Date of Patent: * Mar. 18, 1986

[54] DUAL MODE GAS SAMPLER AND PNEUMATIC FLOW CONTROL SYSTEM

[76] Inventor: Hill S. Lalin, 10 Bonita Ter., Wayne, N.J. 07470

[*] Notice: The portion of the term of this patent subsequent to Aug. 6, 2002 has been disclaimed.

[21] Appl. No.: 612,334

[22] Filed: May 21, 1984

Related U.S. Application Data

[63] Continuation-in-part of Ser. No. 512,935, Jul. 12, 1983, Pat. No. 4,532,814.

[51] Int. Cl.[4] .......................... G01N 1/24; G01N 1/26
[52] U.S. Cl. ............................ 73/863.03; 73/864.34; 73/863.31; 73/863.21; 73/863.23
[58] Field of Search .......... 73/863.03, 863.01, 863.02, 73/863.21, 863.22, 863.23, 863.24, 863.25, 863.31, 864.33, 864.34, 864.35; 417/307, 308, 309, 311; 55/270

[56] References Cited

U.S. PATENT DOCUMENTS

| | | | |
|---|---|---|---|
| 1,873,010 | 8/1932 | Mitton | 73/864.35 |
| 2,819,774 | 1/1958 | Schmidt et al. | 55/270 X |
| 3,343,217 | 9/1967 | Daubenberger | 417/311 X |
| 3,447,360 | 6/1969 | Laseter | 73/863.31 X |
| 3,751,983 | 8/1973 | Rutkowski et al. | 73/864.35 |
| 3,965,747 | 6/1976 | McCorkle | 73/863.02 |
| 4,246,788 | 1/1981 | Olin et al. | 73/863.03 |
| 4,269,059 | 5/1981 | Baker | 73/863.03 |
| 4,288,206 | 9/1981 | Tigwell et al. | 73/863.31 X |
| 4,432,248 | 2/1984 | Lalin | 73/863.03 |
| 4,461,180 | 7/1984 | de Menibus | 73/706 |

FOREIGN PATENT DOCUMENTS

| | | | |
|---|---|---|---|
| 40928 | 12/1981 | European Pat. Off. | 73/864.35 |
| 2053155 | 2/1981 | United Kingdom | 73/863.31 |

OTHER PUBLICATIONS

"Flexible Bags Collect Samples", *Control Engineering;* Sep. 1967; p. 105, F. J. Lourence et al.

*Primary Examiner*—Stewart J. Levy
*Assistant Examiner*—Tom Noland

[57] ABSTRACT

The dual mode gas sampler and pneumatic flow control system of the present invention includes a flow control valve having a manually adjustable flow restricting orifice, a two position mode select valve, a flow controller and a vacuum pump for drawing gas from the atmosphere through a load representing either a single test article with flow being held constant or multiple test articles with pressure held constant. In one position of the mode select switch the flow controller maintains mass flow through the load constant by regulating a supplemental flow of gas from the discharge side of the pump to the suction side of the pump in response to the pressure differential across the flow restricting orifice. In the other position of the dual mode switch the flow controller regulates the supplementary flow of gas from the discharge side to the suction side of the pump in response to the pressure differential across the pump with the flow control valve bypassed.

17 Claims, 4 Drawing Figures

DUAL MODE GAS SAMPLER AND PNEUMATIC FLOW CONTROL SYSTEM

This application is a continuation-in-part of U.S. Ser. No. 512,935 entitled Fluid Sampler and Gas Flow Control System filed on July 12, 1983 and now U.S. Pat. No. 4,532,814.

FIELD OF INVENTION

This invention relates to a gas sampler for collecting gas samples in a collecting device under controlled conditions of either constant gas flow or multiple gas flow constant pressure. The invention also relates to a pneumatic flow control system for maintaining a constant rate of gas flow through a load at a preselected flow rate, over a wide range, substantially independent of variations in the load.

BACKGROUND OF THE INVENTION

CONSTANT FLOW SAMPLING - SINGLE SAMPLE

In the field of environmental hygiene, air sampling is performed regularly to test the air in industrial work environments to determine the degree of exposure to hazardous chemicals. A typical sampling method involves collecting a sample of a test gas such as air by drawing a known volume of the test gas through a collecting device such as a sorbent tube. The sorbent tube may include a solid sorbent capable of trapping and removing chemicals from the air or may include a filter for selectively collecting particulate. The test sample is then analyzed to determine the concentration level of the collected samples of chemical or particulate matter. The method of analysis may involve gas chromatography or atomic adsorption, etc. The analysis is based on a time weighted average over an eight hour work day to determine the concentration level of contaminants in parts per million. For the analysis to be accurate it is essential that sampling of test gas be performed at a constant fluid flow rate which is preselected for the chemical hazard under examination and the particular sorbent tube employed.

Constant flow chemical sampling, i.e., sampling of gases or vapors through a single sample at a constant flow rate, is typically conducted at low flow levels in a flow range typically between 2 to 200 cc per minute depending upon the chemical hazard under analysis. In the sorbent tube sampling method, air is drawn through the sorbent tube by a vacuum pump at a flow rate which must be held constant in order to obtain a meaningful determination of the concentration level of the hazard under test. One currently used technique to assure constant flow is to use a pump and counter in conjunction with a precalibrated known volume of test gas from which the total volume can be derived. This technique is nonetheless susceptible to erroneous results from changes in load pressure, changes in pump volumetric efficiency, valve loading effects, etc. In another type of pump sampling system, air flow is controlled by adjustment of the pump motor speed. One conventional system uses a pressure switch to generate output pulses which vary in duration corresponding to variations in flow rate. The pulsed output is electronically sensed and converted to control signals having an amplitude which varies with pulse duration. The control signals are then used to adjust the pump motor speed. Another known motor speed control system disclosed in applicant's earlier "Hi-Flow" fluid sampling system, now U.S. Pat. No. 4,432,248, utilizes load sensing of the pump motor to adjust motor speed in proportion to the pump load line curve. All known pump sampling systems which control flow by adjustment of pump motor speed produce an air flow with relatively high pulse undulations at the lower end of the flow regime. With a highly pulsed flow it is much more difficult if not impossible to set the flow rate. In fact at low flow rates of the order of 10 cc or below most common flow meters cannot be used to accurately determine or calibrate the flow because of their sensitivity to pulsation. Current state of the art technology requires several pumps to cover the flow range of 10 to 200 cc/min, therefore each pump is extremely limited in its range capability with the pulsation amplified at the lower end of its respective range.

CONSTANT PRESSURE - MULTIPLE SAMPLING

It is often desirable to take multiple test gas samples simultaneously without using a separate sampling pump for each sample. Multiple sampling involves the preparation of a multiple number of sorbent tubes, each of which are ported in series with individual variable restrictors dedicated to each tube station. The pressure across the manifold is maintained constant, thus allowing the flow rate through each sorbent tube to be individually determined by the setting of the individual restrictors in the manifold assembly. This arrangement allows independent control of the flow rates through each sorbent tube, provided that the total flow through all tubes does not exceed the constant pressure delivery capacity of the device.

DUAL MODE SAMPLING

Prior constant mass flow controllers are not adaptable for use in collecting simultaneous and independently settable samples. The gas sampler of the present invention has a dual mode capability permitting the user to readily switch from a constant flow single sample mode of operation to a constant pressure multiple sample mode of operation. This is accomplished in accordance with the present invention using an arrangement that includes a bypass flow controller, a flow metering orifice, a pump and a mode selector valve which in one position provides for constant flow operation and in the other position provides multiple flow constant pressure operation.

For constant mass flow control the gas sampler of the present invention utilizes the principals of operation disclosed in the parent patent application Ser. No. 512,935, the disclosure of which is herein incorporated by reference. As taught in the parent patent application, the flow through a test article connected in series with a vacuum pump and a metering orifice may be held at a constant preselected flow by maintaining a regulated pressure differential across the flow metering orifice. This is accomplished by the controlled addition of a secondary gas stream to supplement the metered gas flow stream drawn by the pump through the test article. The secondary gas stream is regulated by a flow controller connected across the pump and connected to respond to the pressure differential across the metering orifice. The flow controller operates to divert a controlled fraction of the pump total flow from the net pump discharge and to reintroduce it at the pump inlet in combination with the metered mass flow to maintain the mass flow constant. In the parent patent application the flow controller includes a ganged dual diaphragm assembly forming two diaphragm chambers separated by a central plenum chamber with each diaphragm chamber ported through a separate conduit to one side of the metering orifice, a valve assembly responsive to the difference in pressure in each of the diaphragm chambers for controlling the secondary stream and a preloaded spring for adjusting the initial equilibrium condition. In the parent application the flow controller can be placed on the suction or discharge side of the vacuum pump in a series arrangement with the test article and the pump. It has been found in accordance with the present invention that a single diaphragm flow controller may be used to provide the equivalent function of the more complex dual diaphragm controller of the parent application not only for constant flow sampling but also for multiple draw sampling provided that the metering orifice is located on the discharge end of the pump in a series arrangement with the test article and the pump, and that one end of the metering orifice is tied, substantially, to atmospheric pressure. The pressure differential across the metering orifice is then regulated for the purpose of maintaining a constant mass flow through the test article. The suction at the pump inlet is dictated by whatever load or changing load the test article may present. Over a wide range bounded by the intrinsic limits of regulation provided by a given sampler specification or design. The flow controller regulated the supply of secondary gas flow to assure a constant primary mass flow independent of variations in the test article load and at any preselected primary gas flow level over a wide range. Moreover, flow is controlled substantially independent of the pump operating speed and characteristics.

Furthermore, in the constant flow mode of operation the system will automatically compensate for any change in test load to assure a constant flow rate without requiring recalibration each time a new test sorbent tube is introduced into the system. The flow rate is established by adjustment of the metering orifice to a desired flow setting over a wide flow range.

The flow controller in the present application is a miniature structure having a cylindrical cavity with a single flexible diaphragm disposed in the cavity to constitute a common wall for dividing the cavity into a first and second plenum chamber and also includes a preloaded manually adjustable spring extending into one of the chambers in engagement with the diaphragm. The flow controller further includes a valve assembly having a valve head connected to the diaphragm with which it moves freely as one unit to assume a valve displacement dictated by the equilibrium of the preloaded spring acting against the force of the differential pressure across the diaphragm.

SUMMARY OF THE INVENTION

The gas sampler of the present invention is used to collect gas samples in a collecting device under conditions of either constant gas flow or constant pressure. In the broadest sense, the gas sampler comprises: a vacuum pump having a suction and discharge end, a flow control valve having a manually adjustable flow restricting orifice, adapted to be coupled in series with the collecting device and a bypass flow controller for redirecting a secondary supply of gas from the discharge end of the pump to the suction end of the pump. In the constant flow mode of operation the flow controller responds to the pressure difference across the flow control valve to regulate the secondary supply of gas to maintain the mass flow through the collecting device constant independent of load variations.

The gas sampler further includes a mode selector valve which provides for two operating modes, constant flow and constant pressure. In the constant flow mode a single test article is sampled and the system will maintain the flow constant regardless of pressure changes in the test article. In the constant pressure mode the mode selector valve bypasses the flow control valve to reduce the gas sampler to a series arrangement between the pump and collecting device preferably represented for this operation by a common manifold and a multiple number of test articles. The flow controller remains connected across the pump to divert flow from the pump discharge to the pump inlet and is connected, in this mode of operation, through the mode selector valve to respond to the pressure differential across the pump. This arrangement for constant pressure sampling is substantially similar to the regulator and pump arrangement shown and described in applicant's earlier U.S. Pat. No. 4,432,248 entitled Fluid Sampling. The mode selector valve is in itself unique in that it provides for switching the interconnections between the flow control valve, the flow controller and the pump to convert from a constant flow mode of operation to a constant pressure mode of operation and vice versa by means of a single manual rotation of the selector valve rotor. The selector valve is also of miniature size permitting the entire gas sampling system to be housed in a compact miniature case.

The pneumatic flow control system of the present invention for maintaining a constant rate of gas flow through a load at a preselected flow rate within a wide flow range comprises: an adjustable metering orifice for preselecting the flow rate; a pump having a suction and discharge end and connected between the load and metering orifice, with the discharge end adjacent to the metering orifice, for pumping gas from an ambient source of supply through the load and metering orifice in a series flow path, and a flow controller for bypassing a supplementary flow of gas from the pump discharge port to the pump inlet port and being responsive to the pressure differential across the metering orifice to maintain the flow of gas through the load constant.

OBJECTS

It is therefore the principal object of the present invention to provide a gas sampler for collecting gas samples in a test article or articles under controlled conditions of either constant gas flow or constant pressure.

It is a further object of the present invention to provide a gas sampler for collecting a sample of test gas at a constant preselected flow rate over a wide flow range substantially independent of load conditions.

It is another object of the present invention to provide a pneumatic gas flow control system for regulating gas flow through multiple loads at low gas flow rates in a constant pressure sampling mode. This provides a flow stable system provided the pump load pressure is small compared to the control pressure or system pressures.

It is yet another object to provide a gas sampler capable of collecting gas samples at constant flow or at constant pressure through a single manual adjustment of a mode selector valve.

BRIEF DESCRIPTION OF THE DRAWINGS

Other objects and advantages of the present invention will become apparent from the following detailed description of the invention when reading in conjunction with the accompanying drawings of which.

DETAILED DESCRIPTION OF THE INVENTION

Figure 1:
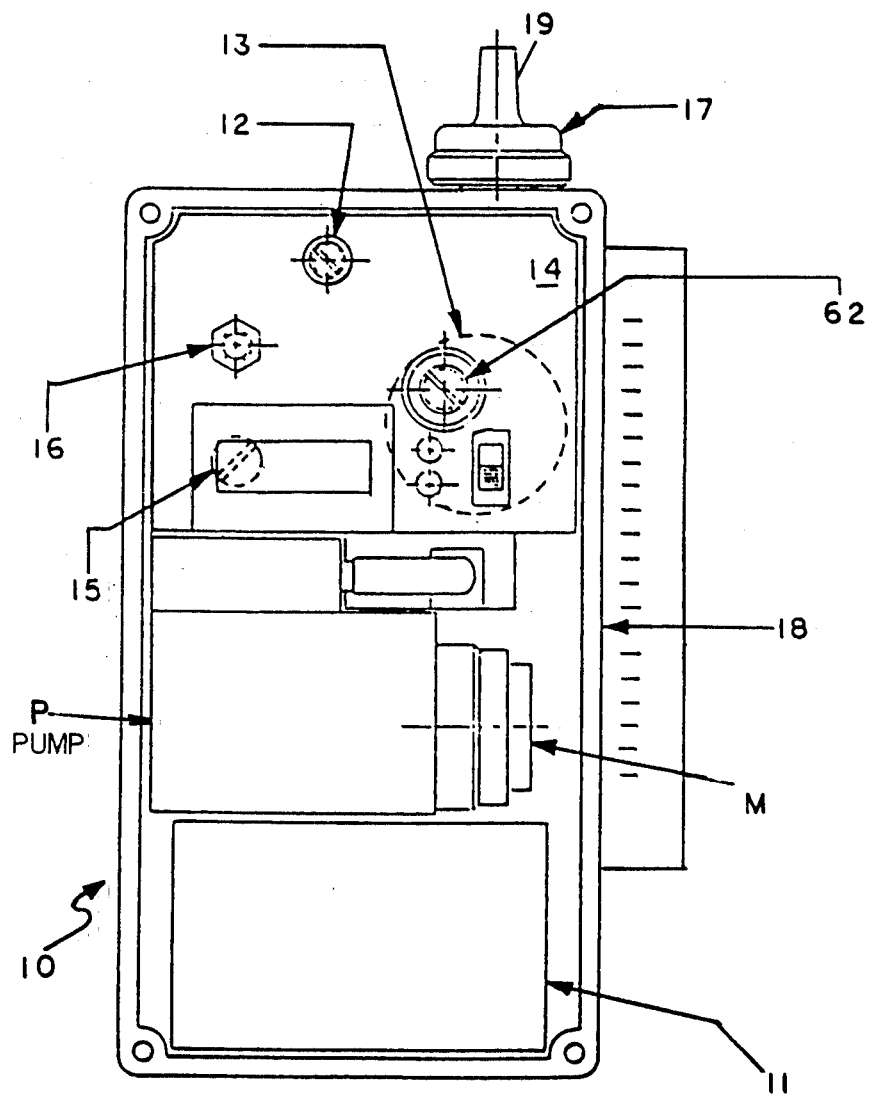
FIG. 1 is a full scale side elevation of the gas sampler and pneumatic flow control system of the present invention.

The gas sampler 10 shown in FIG. 1 includes a pump P, a DC motor M, a battery supply system 11, a flow control valve 12, a flow controller 14, a pressure switch 15, a damper 13, a mode selector valve 16 and a filter assembly 17, all of which are mounted in the case 18. The filter assembly 17 has an air intake boss 19 mounted on the outside of the case 18 and a filter membrane (not shown) to protect the gas sampler 10 from dirt and debris. The pump P may be a conventional single or dual piston diaphragm type pump such as is disclosed in applicant's earlier U.S. Pat. No. 4,432,248. The pump P is driven by the DC motor M which is powered by the battery supply system 11. The battery supply system 11 may consist of a nickel cadmium battery assembly and may further include a battery voltage indicator as well as a timer to indicate hours of operation. The speed of the drive motor M is proportional to the battery supply voltage. The flow envelope characteristic for the pump P is selected to provide the desired operating flow range for low flow air sampling. The vacuum pump P should typically provide a flow characteristic of 200 cc per minute at a minimum back pressure of 40 inches of water.

A collecting device such as a sorbent tube for taking gas samples, preferably of air, is coupled to the inlet boss 19 of the gas sampler 10. A sorbent tube is a cylindrical shaped vial normally filled with a solid sorbent such as granulated charcoal and which is sealed at both ends with breakable end tips. The end tips are broken open when collecting an air sample. The pump P draws air through the sorbent tube at a fixed rate, preset by the manual adjustment of the flow control valve 12. The flow rate is monitored and regulated by the flow controller 14.

Figure 2:
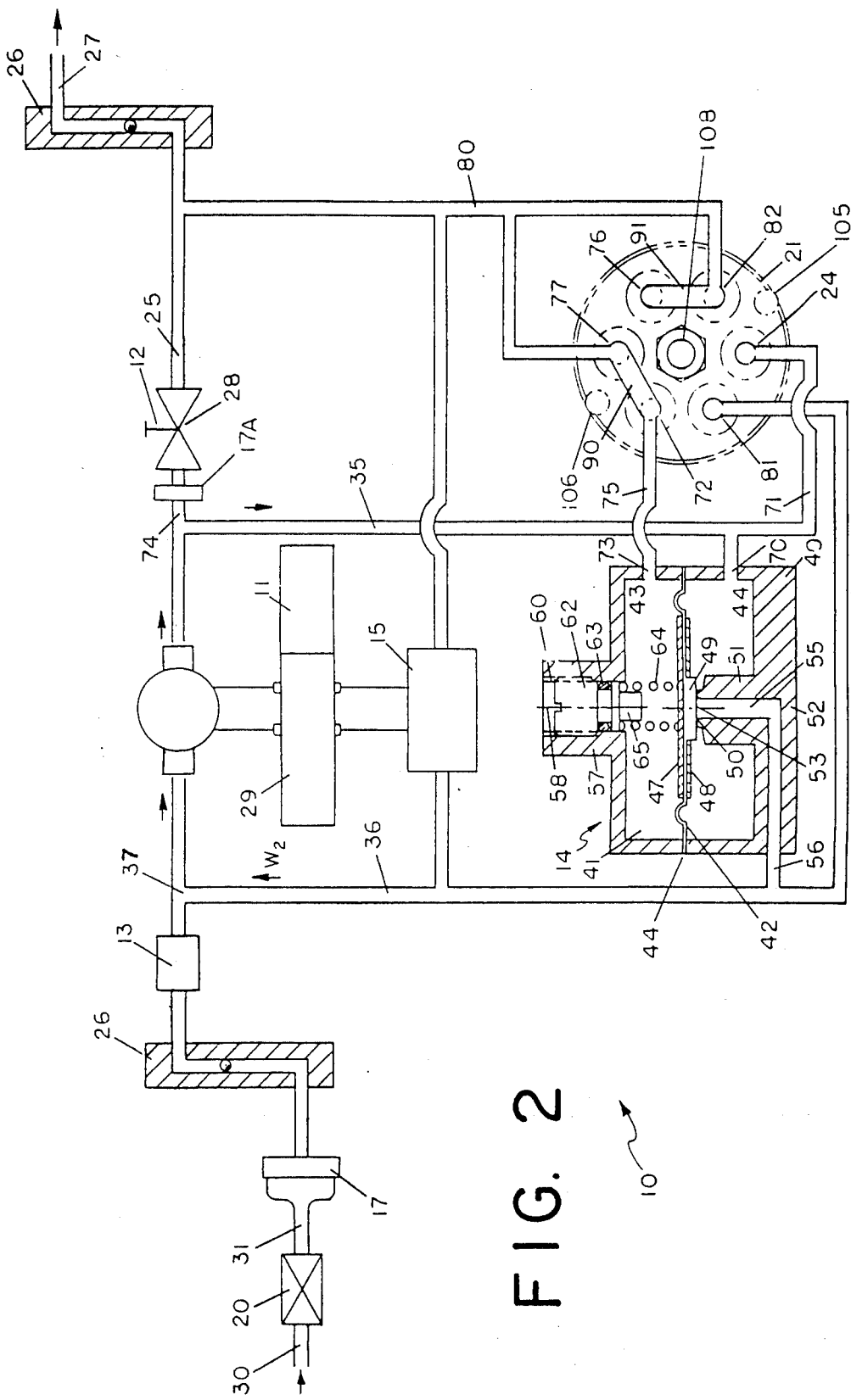
FIG. 2 is a system schematic diagram of the gas sampler of FIG. 1 showing the pneumatic flow control system of the present invention in the constant flow mode of operation.
Figure 3:
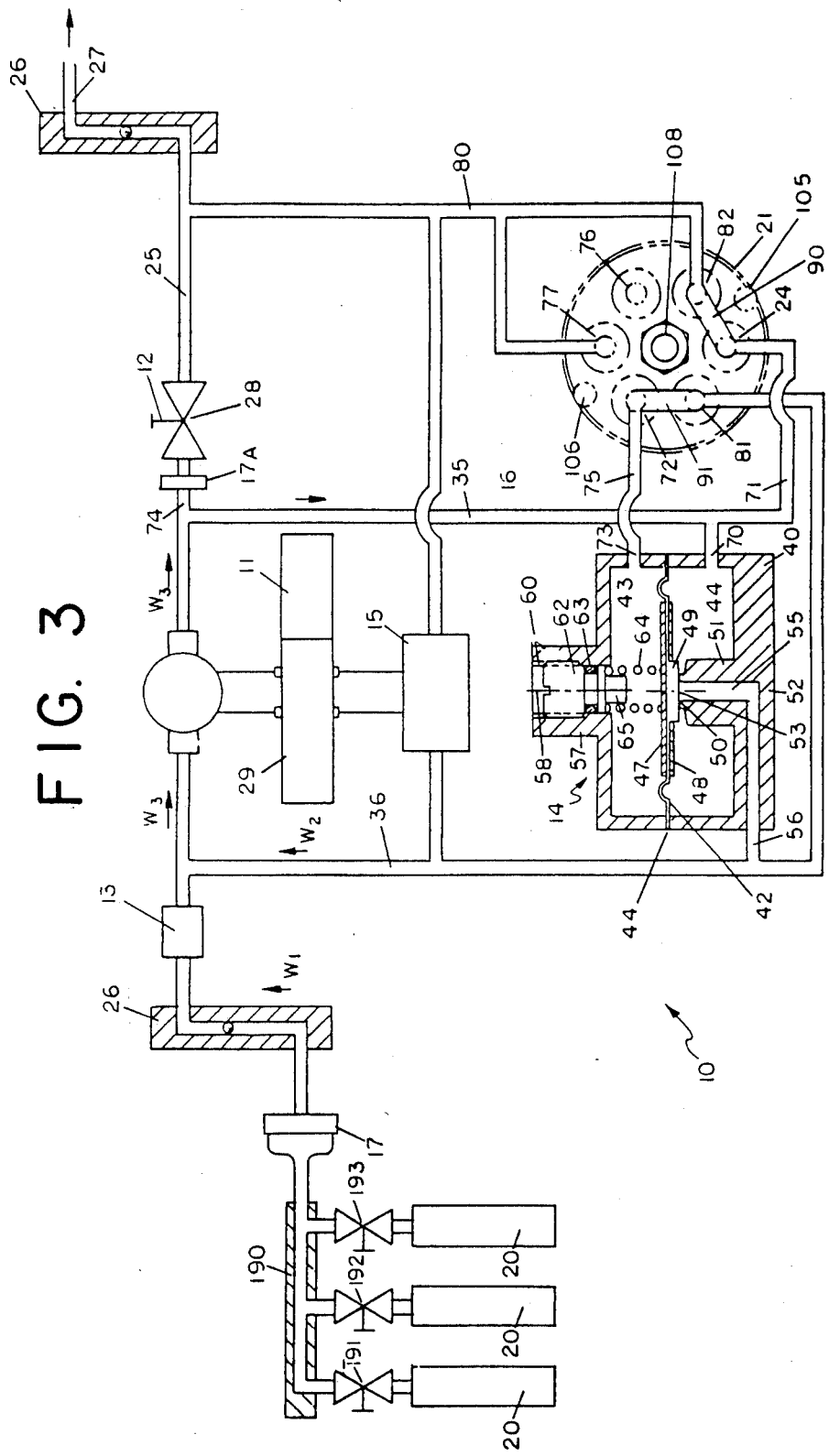
FIG. 3 is a system schematic diagram similar to FIG. 2 showing the pneumatic flow control system in the constant pressure mode of operation.
Figure 4:
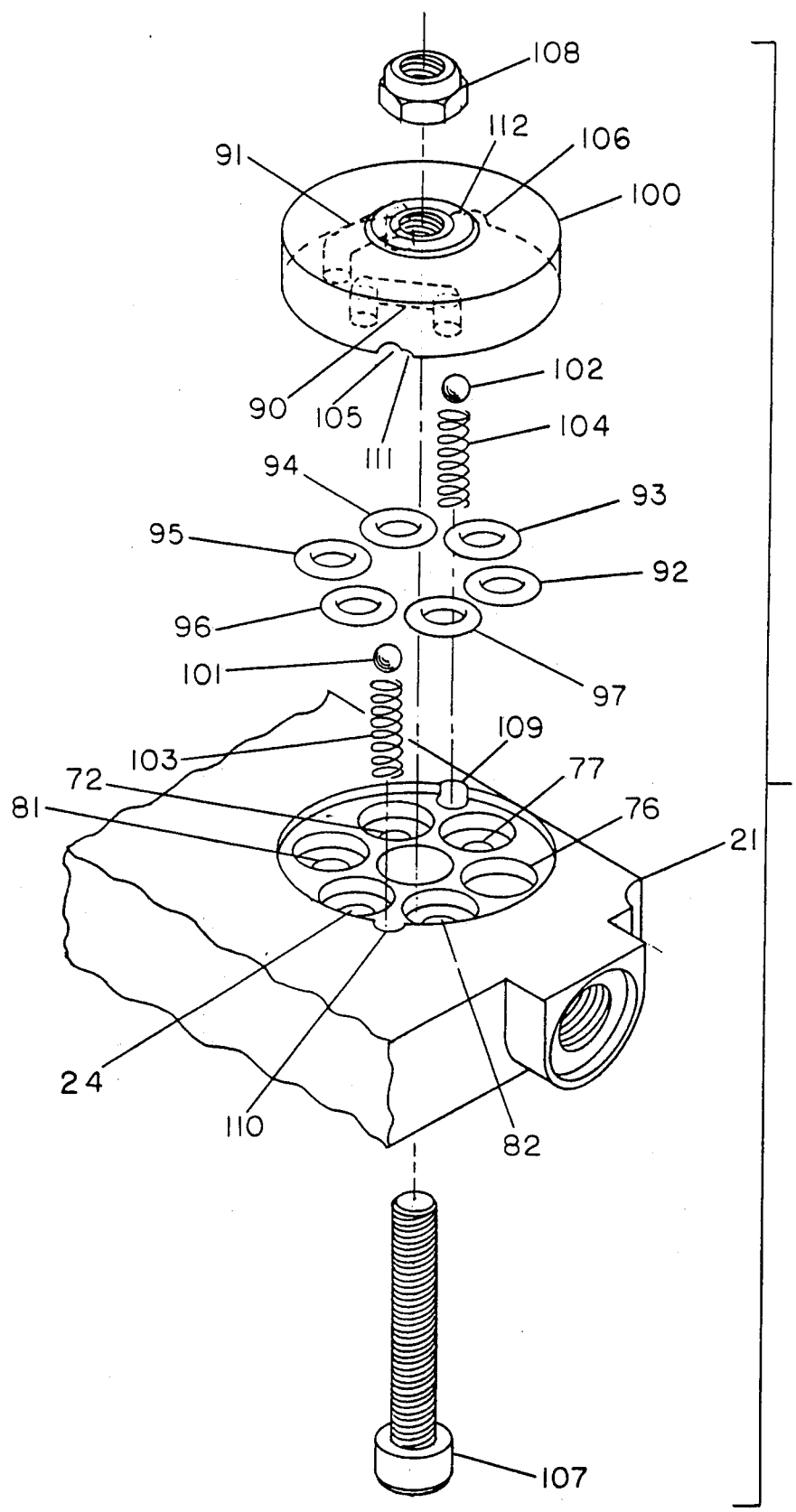
FIG. 4 is an exploded view in isometric of the mode selector valve of FIGS. 2 and 3.

Operation of the gas sampler 10 will now be described in connection with FIGS. 2, 3 and 4 wherein like reference numerals are used to designate the corresponding components. FIG. 2 is a schematic diagram of the gas sampler 10 of FIG. 1 in the constant flow mode of operation. Likewise, FIG. 3 is a schematic diagram of the gas sampler of FIG. 1 in the constant pressure mode of operation.

The test article 20 represents the collecting device (sorbent tube) through which a flow of gas is drawn, preferably from the atmosphere, by the vacuum pump P, at a preset flow rate selected by adjustment of the flow control valve 12. The test article 20 is connected in series with the vacuum pump P and the flow control valve 12, with the test article 20 positioned on the suction side S of the pump P and with the flow control valve 12 positioned on the discharge side D of the pump P. An optional second filter 17A is interposed between the pump discharge D and the flow control valve preventing debris from affecting the setting of the flow control valve. The downstream end 25 of the flow control valve 12 is open to the atmosphere or is connected through an optional flow meter 26 to the atmosphere. Alternatively, for use in a closed loop operation, the open end 27 of the flow meter 26 may be connected back through any ambient source of supply gas (not shown) to the input end 30 of the test article 20.

The filter assembly 17 is connected on the downstream side 31 of the test article 20, upstream of the pump P. A damper 13 is coupled within the series flow path between the test article 20 and the pump P to further reduce pulse flow undulations. The operation of the filter 17 and damper 13 are independent of the pneumatic flow control system of the present invention. The flow meter 26 may be located in the series flow path between the test article 20 and the pump P, directly downstream of the filter assembly 17 instead of the location downstream of the flow control valve 12. The flow meter 26 may represent a vertically mounted conventional rotometer to indicate the preselected level of flow through the test article 20 over the operating range of typically between 2 to 200 cc per minute in the constant flow mode and between 2 to 350 cc per minute in the constant pressure operating mode. The flow rate specified are applicable to the low flow sampler described. However, the system can be scaled to operate at any flow rate.

The manually adjustable flow control valve 12 is a conventional needle valve with an adjustable metering or flow control orifice 28 for establishing a predetermined restriction to flow in the series flow path including, in combination, the test article 20, the filter 17, the damper 13, the pump P, the filter 17A, and the flow control valve 12. The pump P draws air through the test article 20 at a fixed preset flow rate W1 as determined by the manual adjustment of the flow control valve 12.

The flow rate W1 is regulated at the preset constant rate by the bypass flow controller 14. The bypass flow controller 14 is connected across the pump P to divert gas flow W2 from the discharge side D of the pump P and to reintroduce the diverted gas flow W2 into the suction side S of the pump P. The diverted gas flow W2 passes through conduit 35 into the flow controller 14 and through conduit 36 to a junction point 37 on the suction side S of the pump P at which point the flow W2 is added to the flow W1 to form a combined flow W3.

The flow controller 14 is a miniature compact structure having an outer casing 40 with an internal cylindrical cavity 41 which is divided by a flexible diaphragm 42 into two plenum chambers 43 and 44, respectively. The flexible diaphragm 42 is of an elastomeric material having an annular rim held securely in place in an annular groove 44 formed in the outer casing 40. The diaphragm 42 constitutes a common wall for separating the cavity 41 into the two plenum chambers 43 and 44, respectively.

A pair of plates 47 and 48 are mounted on opposite sides of the diaphragm 42. The plates 47 and 48 are preferably of a plastic composition and may be bonded to each opposite side of the diaphragm 42 or may have a tongue and groove configuration (not shown) so that they may be mechanically coupled to each other with the diaphragm 42 sandwiched between them. The bottom plate 48 has a depending pad 49 of elastomeric material which forms a valve piston head. The valve piston head 49 is aligned to register with a valve seat 50 formed as a rounded or dimpled protrusion upon a nozzle 51 projecting from the bottom wall 52 of the casing 40. The valve head 49 and valve seat 50 form a valve assembly. The valve head 49 has a flat surface 53 which engages the valve seat 50 when the valve head is urged into a closed position against the valve seat 50. The nozzle 51 has a central passageway 55 extending through the valve seat 50 and through the bottom wall 52 where it joins a conduit 56 leading into the return conduit 36.

The flow controller 14 has a hollow boss 57 with a bore 58 coaxially aligned with the passageway 55 in the column 51. The bore 58 has a threaded counterbore 60 to receive a manually adjusting screw 62. A spring 64 is mounted with one end about a cylindrical post 65 extending from the screw 62 and with the opposite end seated in a recess in the plate 47. Adjustment of the screw 62 controls the compression of the spring 64 and in turn the loading force applied by the spring against the plate 47 and diaphragm 42.

The chambers 43 and 44 of the flow controller 14 are pressurized to provide a pressure differential across the diaphragm 42 corresponding to the pressure differential across the combination of the flow control valve 12 and the filter 17A. The lower chamber 44 is ported through an opening 70 to a conduit 71 which is coupled through conduit 35 to the discharge sided of the pump P. Accordingly the pressure in the lower plenum chamber 44 is equal to the pressure on the discharge side D of the pump P, which, in this mode, is the same pressure as at the upstream end 74 of the combination of flow control valve 12 and filter 17A.

The mode of operation of the gas sampler 10 is governed by the mode selector valve 16. The mode selector valve 16 as shown in more detail in FIG. 4 includes a base 21 having multiple ports 72, 77, 76, 82, 24 and 81 and a manually adjustable rotor 100. The rotor 100 is mounted above the base 21 with the ports 72, 77, 76, 82, 24, and 81 sealed by O-ring glands 92 through 97. The rotor 100 is rotated from a first position as shown in FIG. 2 defining the constant flow mode of operation to a second position as shown in FIG. 3 defining the constant pressure mode of operation and vice versa. The second position requires a 180 degree rotation of the rotor 100 about its central axis. This is more clearly understood from the assembly drawing of FIG. 4. The rotor 100 is fixed into an operating position only when the spring loaded balls 101 and 102 engage the rotor detents 105 and 106. The springs 103 and 104 are seated in recesses 109 and 110 in the base 21. In this position, the rotor 100 is sealed against the base 21 through the O-ring glands 92-97. The rotor 100 has internal tubulations 90 and 91 which in the position of FIG. 2 interconnect port 72 to port 77 and port 76 to port 82. When the rotor is rotated 180 degrees about its central axis into the position shown in FIG. 3, the internal tubulations 90 and 91 interconnect port 72 to port 81 and port 82 to port 24.

The rotor detents 105 and 106 are configured with adjacent indented surfaces 111 and 112 which function as cams in conjunction with the detents to facilitate locking and unlocking of the rotor 100 with the base 21.

Mode selection is achieved by rotation of the drive screw 107 which lifts the rotor 100 via the spring loaded balls 101 and 102 until the rotor jams against the lock nut 108. Additional turning of the screw 107 will now cause the rotor to deflect the balls into the housing and permit the rotor to rotate 180 degrees into the alternate position with the balls 101 and 102 engaging the detents 106 and 105 respectively. Reversing the screw direction will cause the detents 105 and 106 to prevent the rotor from rotating until the jam nut 108 disengages the rotor. Additional turning of the screw will cause the rotor to seal against the base by deflection of the O-rings 92 through 97.

Port 81 in the mode selector valve 16 is coupled to the suction end of the pump through conduit 36 while port 24 is connected to the pump discharge through conduit 35 and to the lower chamber 44 of the flow controller 14. The ports 77 and 82 are connected in common to the discharge end of the flow control valve 12 through conduit 80. Port 72 is connected to chamber 43 of the flow controller 14 via conduit 75.

In the constant flow mode of operation, ports 82 and 76 are connected through rotor tubulation 91 and ports 72 and 77 are connected via tubulation 90 thereby connecting chamber 43 to the discharge of the flow control valve 12. The supplemental flow W2 is diverted from the discharge end of the pump P and passed through the valve seat 50 into the suction end S of the pump P where it is combined with the flow W1 such that the flow through the pump P is equal to W3. The valve assembly regulates the supplementary flow W2 in response to the summation of forces across the diaphragm 42 resulting in a displacement of the valve pad 49 from the valve seat 50 dictated by the equilibrium between the force applied by the preloaded spring 64 against the force of the differential pressure across the diaphragm and the force applied to the valve pad 49 through the valve seat 50 from the suction end S of the pump P. The equilibrium condition is satisfied when the pressure differential across the flow control valve 12 and, accordingly, between the upper and lower chambers 43 and 44, is restored to a preadjusted constant at the initially established operating condition based on the manual adjustment of the spring 64. The suction at the pump inlet end S of the pump P is dictated by whatever load the test article 20 may present over a wide range including any increased loading resulting from the filter assembly 17.

The flow W1 through the test article 20 will be held constant at the pre-established value determined by adjustment of the flow control valve 12. Once the flow W1 is preset the flow controller 14 will maintain the flow W1 at the preset value independent of changes in load based either on a substitution of the test article 20 or resulting from an increased flow impedance due to dirt or debris in the filter assembly 17 or in the test article 20. The control variable is the secondary flow W2 and the pressure differential across the flow control valve 12 is the regulated medium.

The theory of operation is based on regulating the pressure differential across the flow control valve 12 to a preselected constant and thereby maintaining a constant flow through the test article 20 in series therewith. The expression "maintaining a constant flow" is intended to mean regulated to a value having a close approximation to the initializing condition. The theory underlying the constant flow mode of operation is consistent with the more elaborate explanation in the parent application U.S. Ser. No. 512,935 the disclosure of which is herein incorporated by reference. However, the application of the general principles taught in the parent application, when applied to the pneumatic system of the present invention using a single diaphragm flow controller 24, required placement of the flow control valve 12 on the discharge side of the pump such that the pressure on the downstream side 25 of the flow control valve 12 will be fixed, or essentially fixed, at atmospheric pressure. In this arrangement only one side of the flow control valve 12, viz., the discharge end of the pump P, requires regulation to maintain the differential pressure across the flow control valve constant.

The pressure switch 15 is connected between the conduits 36 and 80 and operates in a conventional manner for the constant flow mode of operation to shut the pump P down by deenergizing the motor M should the total system pressure become higher than that for which the pump capacity is selected, thereby maintaining flow constant so long as the flow is maintained within prescribed limits. The pressure switch 15 may optionally be coupled through a conventional electronic time delay circuit 29 to provide a suitable time delay before deenergizing the motor M.

The constant flow mode of operation is converted to a constant pressure mode of operation by rotating the mode select valve 16 180 degrees into the position of FIG. 3. In the constant pressure mode, the port 24 is connected to the port 82 through rotor tubulation 90 thereby connecting the pump discharge via conduit 35 directly to the discharge of the flow control valve through conduit 80. This functionally removes filter 17A and the flow control valve 12 from the system. In addition port 72 is connected to port 81 through rotor tubulation 91 thereby connecting the upper chamber 43 of the flow controller 14 to the suction side of the pump via conduit 36. The pressure in lower chamber 44 of the flow controller 14 remains equal to the pressure on the discharge side D of the pump which is now at atmospheric pressure or is essentially at atmospheric pressure. The flow controller 14 will now be responsive to the pressure differential across the pump P which is equivalent to the pressure differential across the load since the flow control valve 12 is bypassed. The load for constant pressure operation is represented by a common manifold 190, to which a multiple number of test articles or sampling tubes 20 are connected, and by the filter and damper assemblies 17 and 13, respectively. The sampling tubes 20 are connected to the common manifold 190 through individually controlled metering orifices 191, 192, and 193, respectively. Air is drawn by the pump P through the multiple sampling tubes 20 and through each of the respective metering orifices 191, 192, and 193 into the common manifold 190 from whence the air is drawn through the filter and damper assemblies 17 and 13, into the pump P. The flow controller 14 diverts flow W2 from the pump discharge back into the pump inlet to supplement the flow W1 from the common manifold 190 to maintain the pressure across the pump P at a preselected constant based upon adjustment of the screw 62. It should be clearly understood that in this mode of operation the flow W1 is flow stable but does not remain constant with changes in load. The pneumatic system arrangement in this mode of operation is similar to the fluid sampling disclosed in applicant's predecessor U.S. Pat. No. 4,432,248.

I claim:

1. A pneumtic flow control system for collecting gas samples in a collecting device at a constant preselected flow rate comprising a vacuum pump having a suction side and a discharge side, with said collecting device connected to the suction side of said pump, a flow control valve having a flow restricting orifice with one side connected to the atmosphere and with the other side connected to the discharge side of said pump in series with said pump and said collecting device and a flow controller including means connected across the pump for diverting a supplementary flow of gas from the discharge side of the pump into the pump suction side and valve means responsive to the pressure differential across said flow control valve for regulating said supplementary flow so as to maintain the gas flow rate through said collecting device constant at said preselected flow rate independent of load variations.

2. A pneumatic flow control system as defined in claim 1 wherein said flow control valve is manually adjustable for varying the size of said flow restricting orifice in order to preset said flow rate through said collecting device.

3. A pneumatic flow control system as defined in claim 2 wherein said flow controller further comprises a hollow casing, a flexible diaphragm assembly separating the hollow casing into a first and second plenum chamber, means for coupling said first plenum chamber to the flow control valve on the discharge side of the pump, means for coupling said second plenum chamber to the opposite side of said flow control valve such that it is at substantially atmospheric pressure, spring means extending into said second plenum chamber in engagement with said diaphragm for applying a predetermined spring force and wherein said valve means is responsive to the pressure differential between said first and second plenum chamber and to said spring force for regulating said supplementary flow of gas through said first plenum chamber into the suction side of said pump.

4. A pneumatic flow control system as defined in claim 3 wherein said spring means is adjustable for varying said spring force upon said diaphragm.

5. A pneumatic flow control system as defined in claim 4 further comprising switch means for connecting the upstream end of the flow control valve to the downwstream end of the flow control valve thereby functionally shorting the flow control valve from the control system and for switching the second plenum chamber to the suction side of the pump thereby converting the control system from constant flow control to constant pressure control.

6. A pneumatic flow control system as defined in claim 3 wherein said valve means comprises a valve pad extending from said diaphragm and a hollow valve seat disposed in said first plenum chamber in registration with said valve pad.

7. A pneumatic flow control system as defined in claim 6 wherein said valve pad has a flat surface engaging the valve seat in the closed valve position.

8. A pneumatic flow control system as defined in claim 7 wherein said valve seat has a dimpled annular protrusion for engaging the flat surface of said valve pad in the closed valve position.

9. A dual mode gas sampler for collecting gas samples in a load represented either by a single test article or a multiple number of test articles comprising: a vacuum pump having a suction side and a discharge side, a flow control valve having a flow restricting orifice connected on the discharge side of the pump in series with said pump and said load, a flow controller connected across said pump for diverting a supplementary flow of gas from the discharge side of the pump to the suction side including valve means within said flow controller for regulating said supplementary flow and a mode selector valve having a first position for coupling said flow controller across said flow control valve such that said valve means regulates said supplementary flow in response to the pressure differential across said flow control valve to provide a constant gas flow through said load and a second position for bypassing said flow control valve and for connecting said flow controller across said pump such that said valve means regulates said supplementary flow in response to the pressure differential across said pump to provide a constant pressure across said load.

10. A dual mode gas sampler as defined in claim 9 wherein said flow controller further comprises a hollow casing and a diaphragm assembly separating the casing into a first and second plenum chamber, spring means extending into said second plenum chamber in engagement with said diaphragm assembly and conduit means for coupling said first and second plenum chambers to said mode selector valve.

11. A dual mode gas sampler as defined in claim 10 wherein said valve means comprises a valve pad extending from said diaphragm and a hollow valve seat disposed in said first plenum chamber in registration with said valve pad and coupled to the suction side of the pump for regulating the supplementary flow from the first plenum chamber into the valve seat.

12. A dual mode gas sampler as defined in claim 11 wherein when said mode select valve is in said first position said second plenum chamber is connected through said mode select valve to the upstream side of said flow control valve at substantially atmospheric pressure and said first plenum chamber is connected to the discharge side of said pump.

13. A dual mode gas sampler as defined in claim 12 wherein said load is a single test article and the flow therethrough is regulated at a preselected flow rate based upon the size of said flow restricting orifice.

14. A dual mode gas sampler as defined in claim 11 wherein when said mode select valve is in the second position said second plenum chamber is connected through said mode select valve to the suction side of said pump and wherein said first plenum chamber remains connected to the discharge side of the pump.

15. A dual mode gas sampler as defined in claim 14 wherein said load is a multiple number of test articles connected to a common manifold with the pressure across said manifold being constant.

16. A dual mode gas sampler as defined in claim 9 wherein said mode selector valve comprises a base having a multiple number of ports and a manually rotatable rotor having internal tubulations which in one position of the rotor interconnects a first predetermined set of said ports to couple said flow controller across said flow control valve and in another position interconnects a second predetermined set of ports to bypass said flow controller.

17. A dual mode gas sampler as defined in claim 16 wherein said mode selector valve further comprises detents in said rotor and spring loaded balls arranged in said base to provide controlled rotation between said two positions.

* * * * *